United States Patent [19]

Ford et al.

[11] Patent Number: 4,617,418

[45] Date of Patent: * Oct. 14, 1986

[54] POLYALKYLENE POLYAMINES VIA VAPOR PHASE REACTION

[75] Inventors: Michael E. Ford, Center Valley; Thomas A. Johnson, Orefield, both of Pa.

[73] Assignee: Air Products and Chemicals, Inc., Allentown, Pa.

[*] Notice: The portion of the term of this patent subsequent to Jul. 31, 2001 has been disclaimed.

[21] Appl. No.: 674,611

[22] Filed: Nov. 26, 1984

[51] Int. Cl.[4] ............................................. C07C 85/06
[52] U.S. Cl. ..................................... 564/479; 564/512
[58] Field of Search ................................ 564/479, 512

[56] References Cited

U.S. PATENT DOCUMENTS

| | | | |
|---|---|---|---|
| 3,121,115 | 2/1984 | Meuly et al. | 564/479 |
| 3,714,259 | 1/1973 | Lichtenwalter et al. | 564/479 |
| 4,036,881 | 7/1977 | Brennan et al. | 564/479 |
| 4,044,053 | 8/1977 | Brennan et al. | 564/479 |
| 4,314,083 | 2/1982 | Ford et al. | 564/479 |
| 4,324,917 | 4/1982 | McConnell | 564/479 |
| 4,362,886 | 7/1982 | Ford et al. | 564/479 |
| 4,394,524 | 7/1983 | Ford et al. | 564/479 |
| 4,399,308 | 8/1983 | Ford et al. | 564/479 |
| 4,463,193 | 7/1984 | Johnson et al. | 564/479 |

FOREIGN PATENT DOCUMENTS

| | | | |
|---|---|---|---|
| 0078000 | 5/1983 | European Pat. Off. | 564/479 |
| 0093434 | 11/1983 | European Pat. Off. | 564/512 |

*Primary Examiner*—Charles F. Warren
*Assistant Examiner*—John A. Sopp
*Attorney, Agent, or Firm*—Russell L. Brewer; E. Eugene Innis; James C. Simmons

[57] ABSTRACT

This invention pertains to an improved process for preparing noncyclic polyalkylene polyamine compounds in high selectivity by reacting ammonia, an alkanolamine and an alkylene amine in the presence of an acidic catalyst. The improvement resides in effecting the reaction under fixed bed catalytic conditions and maintaining the reaction conditions such that a vapor phase condition exists for the reaction mixture comprising both reactants and products. To accomplish the formation of vapor phase conditions, sufficient ammonia is injected into the feedstream along with alkanolamine and alkylene amine so that the dew point temperature of the reaction product mix is below the reaction temperature at reaction pressure.

29 Claims, 6 Drawing Figures

FIG. 1

DEW POINT VARIATION WITH PRESSURE (E/R=2, MELA Conv = 32.95%)

FIG. 2

DEW POINT VARIATION WITH PRESSURE (E/R=2, MELA Conv = 50.93%)

FIG. 3

DEW POINT VARIATION WITH PRESSURE (E/R = 2, MELA Conv = 71.17%)

FIG. 4

DEW POINT VARIATION WITH PRESSURE (E/R = 4, MELA Conv = 36.1%)

FIG. 5

DEW POINT VARIATION WITH PRESSURE (E/R = 4, MELA Conv = 50%)

FIG. 6

DEW POINT VARIATION WITH PRESSURE (E/R = 4, MELA Conv = 86.5%)

POLYALKYLENE POLYAMINES VIA VAPOR PHASE REACTION

BACKGROUND OF THE INVENTION

The condensation of a hydroxy-containing compound with an amine to liberate water is well known. In many instances, the condensation has been effected by using an acid catalyst, such as a phosphorus-containing compound. The ability to effect intermolecular condensation of a hydroxy-containing compound with an amine has been of substantial interest in the preparation of polyalkylene polyamines, particularly polyethylene polyamines.

A variety of polyalkylene polyamines can be formed by the basic reaction of the hydroxy compound and amine compound. However, one of the objectives in the preparation of polyalkylene polyamines has been to maximize the intermolecular condensation to form the linear or noncyclic polyalkylene polyamine as opposed to effecting an intramolecular condensation of such compounds which convert to the cyclic amine. The former amines are utilized in preparing lubricant formulations, acid gas scrubbing compositions, and the like. Numerous patents have issued since the 1960's which illustrate various embodiments for preparing linear polyalkylene polyamines in high selectivity by reacting an alkylene amine and an alkanolamine in the presence of an acidic catalyst. Representative patents include:

Meuly, U.S. Pat. No. 3,121,115, discloses the reaction of an amine with an alkanolamine in the presence of a phosphorus-containing compound to produce alkylated amines. Reaction conditions used were 200°-350° C. and pressures ranged from atmospheric to super atmospheric.

U.S. Pat. No. 4,036,881 discloses the preparation of polyalkylene polyamines, particularly polyethylene polyamines, by the reaction of monoethanolamine and ethylenediamine under liquid phase conditions. An acidic phosphorus-containing compound was utilized to effect catalysis of the reaction. Representative catalyst systems included alkyl and aryl phosphinic acids, phosphoric and phosphorous acid compounds and their anhydrides, and metal phosphates such as iron, aluminum and boron phosphate and so forth. The patentees pointed out that it was important to maintain liquid phase conditions in the reaction zone for achieving high selectivity to linear polyethylene polyamines. If vapor phase conditions were encountered, as shown in Example 12, then selectivity to linear polyethylene polyamines was sacrificed.

Other patents which show the preparation of polyethylene polyamines or broadly, polyalkylene polyamines under liquid phase conditions include U.S. Pat. No. 4,394,524; 4,399,308; 4,362,886; 4,314,083; and European patent application Nos. 0,093,434 and 0,093,983.

The above patents describe various processes for producing polyalkylene polyamines using a variety of acidic catalytic systems such as, for example, Lewis acids, arsenic, antimony or bismuth salts; a variety of phosphorus containing catalyst systems including phosphoric acid, boron phosphate as noted in the Brennan, et al., U.S. Pat. No. 4,036,881, and phosphoramides. Each of the processes involves the reaction of an alkanolamine with an alkylene amine compound at temperatures from about 175°-300° C., and preferably temperatures in excess of 225° C. to produce linear polyalkylene polyamines. Each of the processes employs conditions which maintain the reactants in liquid phase, and thus the reaction pressure is controlled to the extent necessary to maintain such liquid phase conditions at reaction temperature.

U.S. Pat. No. 4,394,524 differs slightly from the processes described above in that ammonia is included as an additional reactant to convert alkanolamine to an alkylene amine in situ. With the utilization of ammonia, higher selectivities to polyethylene polyamines were reported. However, pressures were maintained such that the reaction was carried out in essentially liquid phase.

Although the above liquid phase processes result in producing linear polyalkylene polyamines in relatively high selectivity, the processes suffer from a series of processing disadvantages. The processing disadvantages arise because of the solubility of the catalyst systems in the reactants or reaction byproducts. This is particularly true in the case of phosphorous-containing catalytic compounds in that high proportions of phosphorous are recovered in the reaction product and must be removed. This is typically done by distillation. An additional problem associated with these processes is that the catalyst must be continually replaced or replenished.

SUMMARY OF THE INVENTION

This invention relates to an improvement in a process for producing noncyclic polyalkylene polyamines in high selectivity. The basic process comprises:

contacting (a) ammonia, (b) an alkylene amine compound having two primary amino groups with the general formula:

wherein R is hydrogen or a lower alkyl ($C_1$–$C_4$) radical:
X is a number from 2 to about 6; and
Y is a number from 1 to about 4; with
(c) an alkanolamine compound having primary or secondary hydroxyl groups of the general formula:

wherein R is hydrogen or a lower alkyl ($C_1$–$C_4$) radical;
X is a number from 2 to about 6; and
Y is a number from 0 to about 3.

This contacting is carried out in the presence of an effective amount of an acidic catalyst system, and at a temperature sufficient to effect reaction between the ammonia, alkylene amine compound and alkanolamine compound. The improvement in the basic process and constituting the invention comprises:

passing the reactants into a catalytic reactor packed with a solid phase acidic catalyst;

effecting the reaction under conditions such that the reactor contents remain essentially in the vapor phase, said reaction being carried out within a temperature range from about 200°-285° C., and within a pressure range from about 75 to 275 psig. Vapor phase conditions are maintained within the temperature and pressure range by adding sufficient ammonia into the reaction zone to lower the dew point temperature of the reactor contents in the reaction zone to a level lower than said reaction temperature.

There are numerous advantages associated with the practice of this invention. One of the advantages is that there is no need for catalyst separation from the reaction product in view of the low concentration of catalyst material therein. Another is that the process readily lends itself to continuous operation. A third advantage is that the reaction can be carried out at relatively low pressures, at least lower than those required for many liquid phase conditions thus providing for energy savings. A fourth is that one can achieve very high selectivity to linear polyalkylene polyamines. A fifth is that the process can be carried out using the same catalyst for extending periods of time.

DETAILED DESCRIPTION OF THE INVENTION

The invention relates to a process for synthesizing noncyclic polyalkylene polyamines and preferably linear and branched polyethylene polyamines, such as diethylene triamine and higher homologues. In the process, an alkylene amine having two primary amino groups and, preferably, an unbranched alkylene moiety, such as ethylene diamine is reacted with ammonia and an alkanolamine having a primary or a secondary hydroxy moiety and a primary amino group. The alkylene amine reactants which typically can be used in practicing the process are represented by the general formula:

wherein R is a hydrogen or a lower alkyl; (C$_1$-C$_4$) radical;

X is a number from 2 to about 6; and

Y is a number from 1 to about 4.

A preferred R radical is hydrogen, while the x value is 2 and the y value is 1. Examples of alkyleneamine compounds suited for the reaction include 1,3-propylene diamine, 1,2-propylene diamine, diethylene triamine, triethylene tetramine and ethylene diamine. The latter diamine is the preferred alkylene amine compound for preparing linear polyethylene polyamines.

The alkanolamine reactants which can be used in the process and represented by the formula:

wherein R is hydrogen or a lower alkyl (C$_1$-C$_4$) radical;

x is a number from 2 to about 6, and y is a number from 0 to 3.

A preferred R radical is hydrogen while x is 2 and y is 0. Examples of alkanolamine compounds suited for practicing the process are monoethanolamine, isomeric propanolamines, and N-(2)-aminoethyl(ethanolamine). Monoethanolamine is preferred.

Linear and branched polyalkylene polyamines that are produced by the reaction of ammonia, an alkylene amine and an alkanolamine as described above, are represented by the general formula:

wherein R is a hydrogen or a lower alkyl (C$_1$-C$_4$) radical, preferably a methyl radical;

x is a number from 2 to about 6;

y is a number from 2 to about 6 and

X may vary for a given value of Y.

Examples of linear polyalkylene polyamines that are produced in accordance with the process of this invention include dipropylene triamine, tributylene tetramine and various polyethylene polyamines such as diethylene diamine, triethylene tetramine and tetraethylene pentamine. Other types of polyamines include di(2-methylethylene) triamine, tri(2-methylethylene) tetramine and N-(2-aminoethyl)-1,3-propylene diamine.

A variety of acidic catalytic systems can be utilized for effecting condensation of the hydroxyl group of the alkanolamine with the alkylene amine compound and numerous catalytic systems have already been described in the Background Portion of this Application and such catalysts are incorporated by reference; i.e., from U.S. Pat. No. 4,036,881; European Pat. No. 0 093 434 and U.S. Pat. No. 4,394,524. In view of the fact that the reaction is carried out under vapor phase conditions, the catalyst is material capable of being compounded as a particulate material or capable of being supported by a solid phase carrier. The nonvolatile catalytic systems may be incorporated upon or impregnated into an inert support. Silica, carbon or zeolite are representative of the latter. By utilizing a catalyst system, which is in solid phase form, a fixed bed catalytic reactor can be utilized to effect the condensation of the alkanolamine, alkylene amine and ammonia reactant system.

Catalyst systems suited for effecting intermolecular condensation include the phosphorus containing compounds such as boron phosphate, aluminum phosphate, phosphoric acid on silica or carbon, rare earth metal acid phosphates such as lanthanum acid/phosphates, yttrium acid phosphates, gadolinium acid phosphates, thorium acid phosphates, neodymium acid phosphates, praseodymium acid phosphates, samarium acid phosphates or mixtures of lanthanum acid phosphate with other rare earth metal acid phosphates. The rare earth metals suited are scandium, yttrium, lanthanum, and those in the lanthanide series of the periodic table having an atomic number from 59-71 and the rare earth actinides having atomic numbers 89 to 92. Such catalysts are shown in U.S. Pat.No. 4,463,193 and are incorporated by reference. Rare earth and hydrogen exchanged zeolites can be used provided the cage structure is sufficiently large; e.g., greater than about 8 A° to permit formation of the amine. Other catalytic systems include halide salts such as zinc chloride, the sulfur and nitrogen containing acids and salts such as nitric acid, sulfuric acid, beryllum sulfate, ammonium nitrate, etc. These catalysts can be used so long as they are effective as solid phase catalysts under the conditions specified in the reaction zone for effecting condensation. Antimony, bismuth and arsenic salts can also be used.

The basic difference between this process and the processes described and utilized heretofore in the preparation of polyalkylene polyamines resides in the injection of sufficient ammonia into the reaction system and the maintainance of an appropriate temperature and pressure commensurate with the level of ammonia in the reaction zone such that the mixture of reactants and reaction products are maintained in the vapor phase. If liquid phase conditions are encountered in the reaction zone, then the concentration of catalyst in the reaction product leaving the reactor may increase substantially, particularly when a phosphate system is used, and catalyst must be replaced in the reactor. In addition the catalyst may agglomerate and plug the reactor.

In order to achieve high selectivity to linear or branched polyalkylene polyamines under vapor phase conditions the reaction temperature must be at a temperature above the dew point temperature of the reactor contents but at a temperature less than 285° C. Although the condensation reaction can be effected at temperatures above 285° C., as indicated in the prior art, selectivity to linear polyalkylene polyamines decreases substantially as the temperature is increased above that level when using vapor phase conditions. Even adding more reactant ammonia has little effect or selectivity above that temperature. The lowest temperature suited for practicing invention is that temperature at which the catalyst is catalytically effective for generating polyalkylene polyamines via the intermolecular condensation of the alkanolamine and alkylene amine.

The condensation reaction is carried out at pressure sufficient to effect the reaction of ammonia and alkanolamine with the alkylene amine. More particularly the pressure should be sufficiently low such that the ammonia level does not have to be unreasonably high to maintain vapor phase conditions. Typically the pressure will range from about 75 to 275 psig. Higher pressures serve no useful purpose and tend to require increased ammonia levels at a preselected reaction temperature to maintain vapor phase conditions.

The generation of vapor phase conditions in the process, with concomitant high selectivity to linear polyalkylene polyamines is unique. In the prior art, as exemplified by Brennen, et al. in U.S. Pat. No. 4,036,881, selectivity to linear polyalkylene polyamines was sacrificed when vapor phase conditions were employed in the reaction of monoethanolamine and ethylene diamine. Although not intending to be bound by theory, it is belived there are two primary reasons for high selectivity to cyclics in the Brennen et al example. First the reaction was carried out at too high of a process temperature and second the process pressure was too low. Such conditions were required under those conditions because of the exclusive usage of ethylenediamine and monoethanolamine as feeds and the maintenance of vapor phase conditions. On the other hand in accordance with the invention described here, ammonia is introduced into the reaction zone until the dew point temperature of the components of the reaction zone is below a preselected reaction temperature at reaction pressure. By increasing the amount of ammonia in the reaction zone one can then lower the dew point temperature of the contents in the reaction zone and thereby establish a condition in which vapor phase conditions exist throughout the process. The selection of pressure, temperature and reactants then permits one to achieve high selectivity typically achieved previously only under liquid phase conditions.

Dew point temperatures can be derived from vapor-liquid equilibria for feed and products at various conditions. These vapor-liquid equilibria can be calculated using standard chemical engineering techniques. For example the following articles can be reviewed for producing computer or mathematical models for calculating specific temperature conditions. These articles are:

1. Zellner, et al., Industrial Engineering Chemical Fundamentals, Vol. 9, Nov. 9, 549-564 (1970);
2. Abrams, et al., AICHE Journal, Vol. 21, No. 116-128 (1975).

Both of these articles are incorporated by reference.

Figure 1:
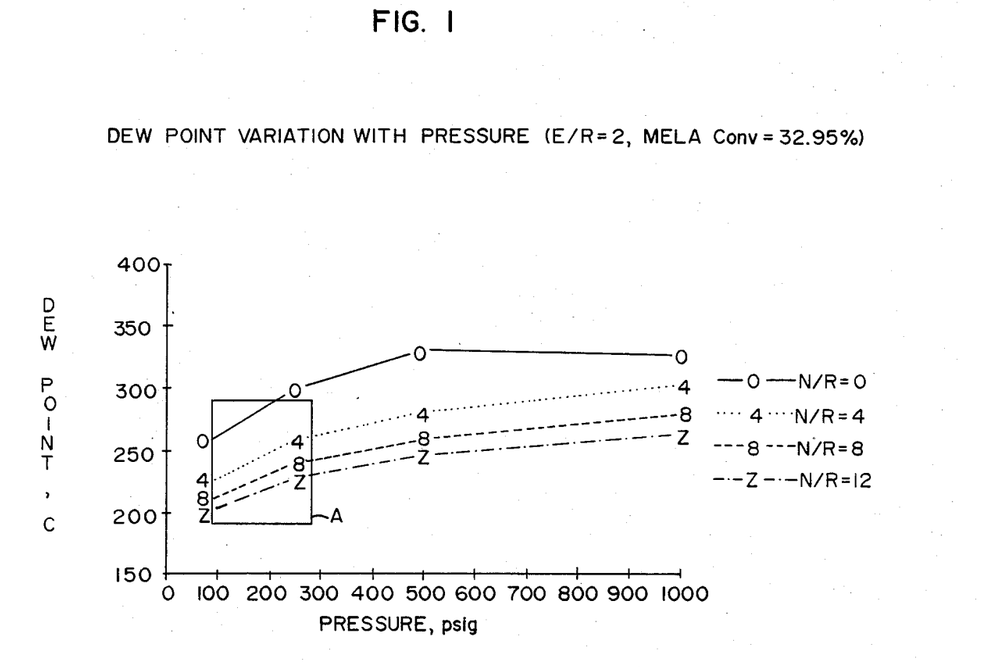
FIGS. 1-6 are dew point temperature diagrams wherein dew point temperature is plotted at various molar reactant ratios of ethylene diamine (E) to monoethanolamine (R) to ammonia (N) and conversions for a range of pressures.
Figure 2:
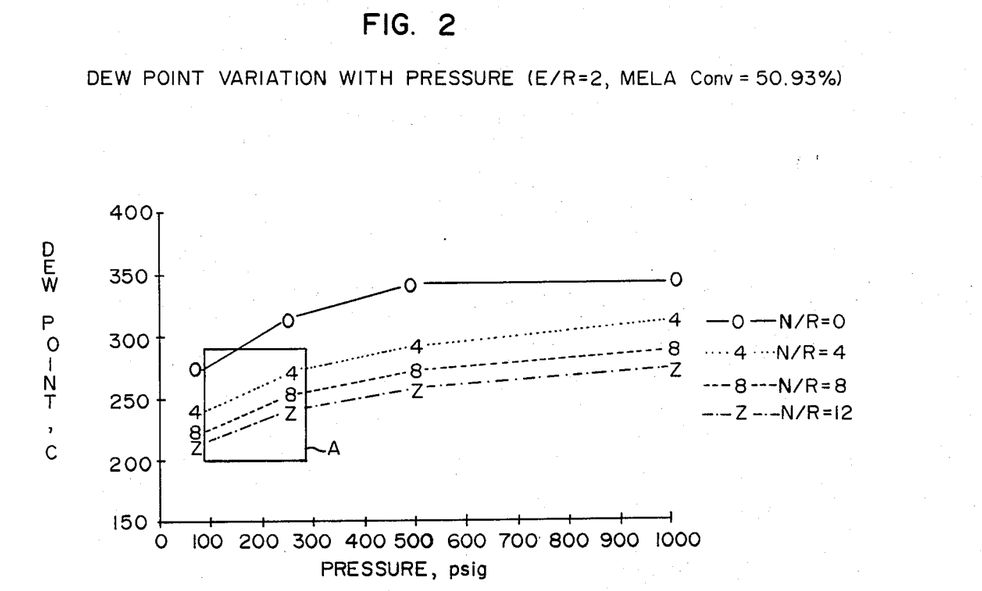
Figure 3:
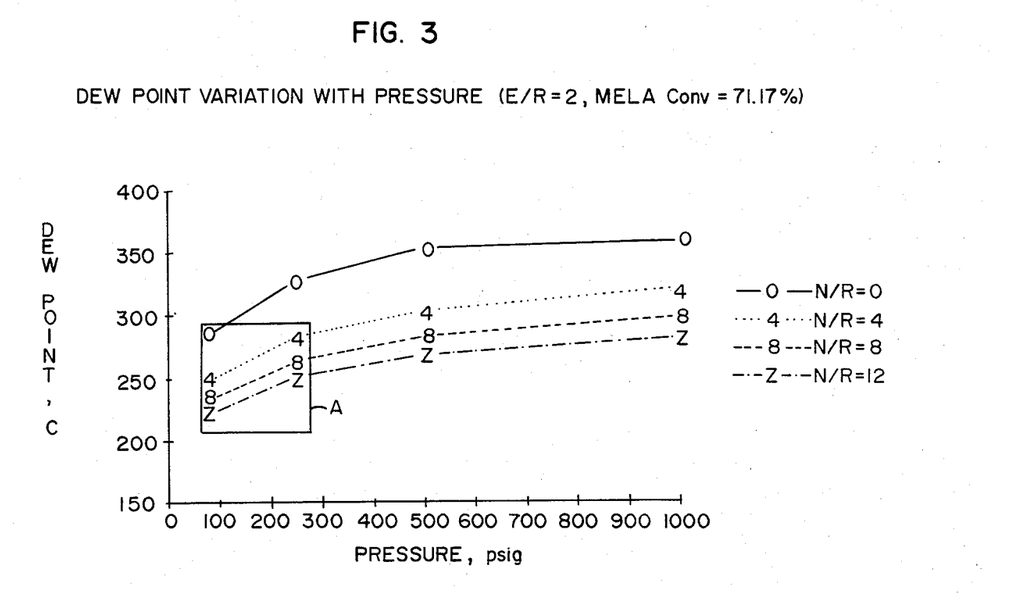
Figure 4:
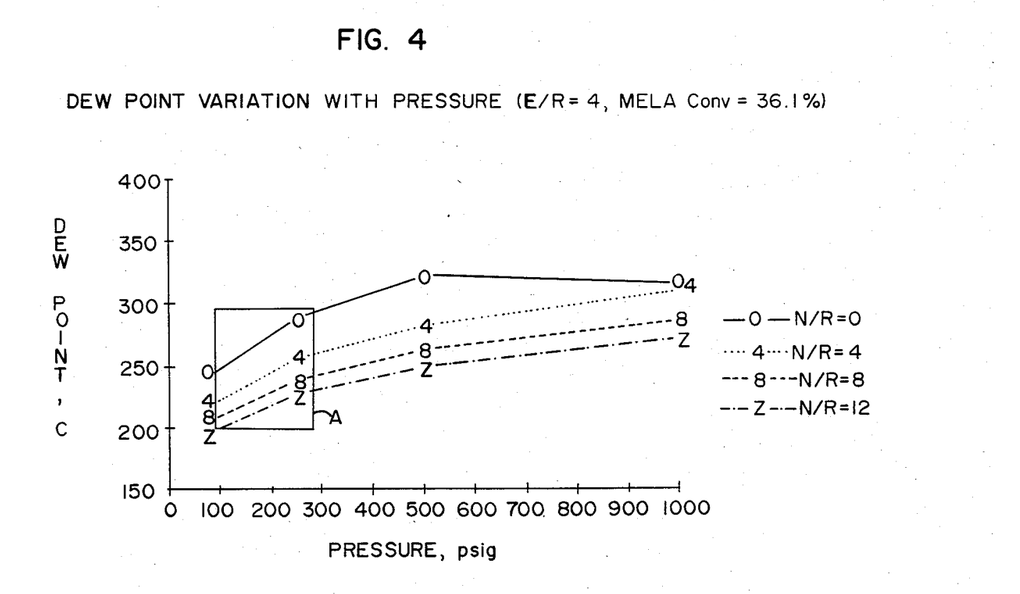
Figure 5:
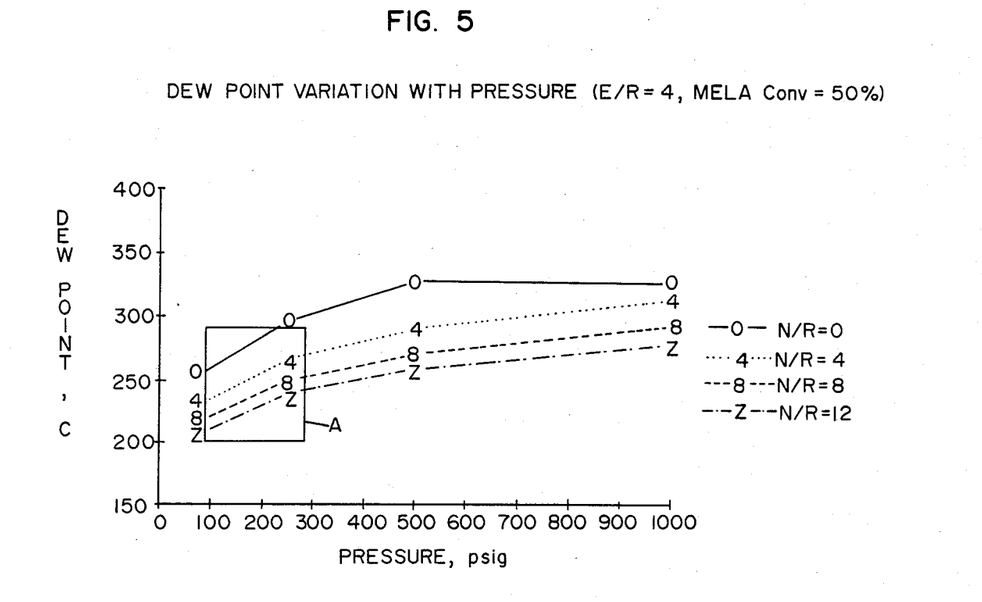
Figure 6:
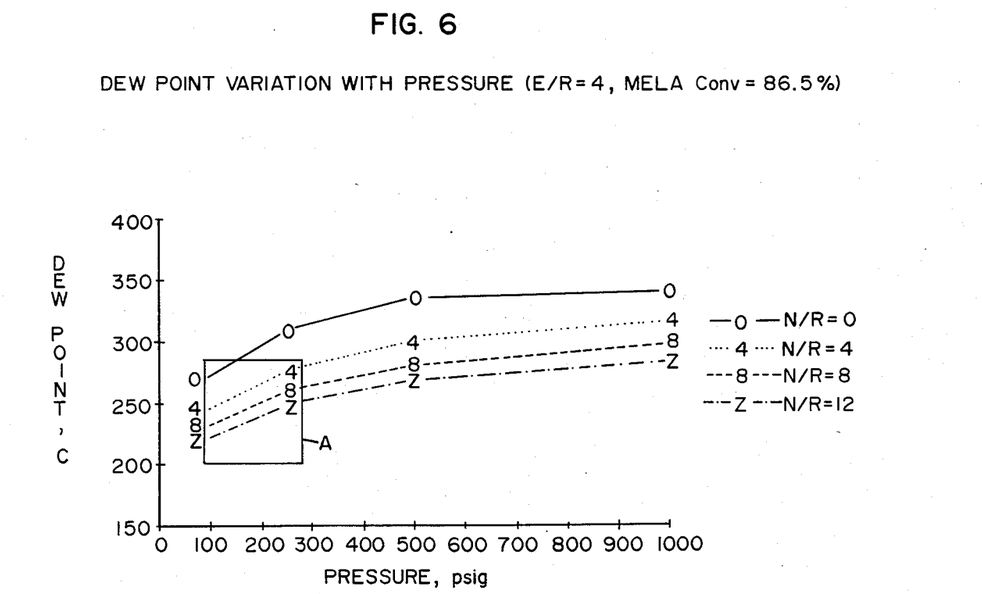

To alleviate some of the necessity for calculations, FIGS. 1-6 have been provided showing correlations between dew point temperature and conversion based upon monoethanolamine for both the polyalkylene polyamine feeds and reactant products at specific pressures. The systems shown are specifically designed for the production of polyethylene polyamines from ethylene diamine (E), monoethanolamine (R) and ammonia (N). In these systems the mole ratio of ammonia to monoethanolamine (N/R) has also been varied and plotted with respect to dew point temperature to provide representative parameters in which to operate. If other reactants are employed then these correlations would not hold and calculations for dew point temperature would have to be made. It also follows that additional calculations would have to be made if conversion levels are significantly different than the levels shown in the drawings.

FIGS. 1-6 are plots of dewpoint temperatures versus pressure. The plots have been constructed based upon ethylene diamine to monoethanolamine molar ratios of 2 and 4:1. The dewpoint temperatures have been calculated at an assumed ammonia to monoethanolamine molar ratio of from 0 to 12:1. Typical operating parameters within a reaction temperature of from 200°-285° C. and 75 to 275 psig, identified as block A have been constructed over these curves to aid in determing the operable conditions to maintain vapor phase conditions. As can be seen from FIGS. 1-6 only a small area of operation is available when no ammonia is introduced into the system and then conversion must also be low.

There are some general principles which apply in aiding the determination of a set of conditions for vapor phase operation. First, the dew point temperature decreases with increasing mole ratios of ammonia to monoethanolamine. Second, the dew point temperature increases as conversion of reactant to produce increases. Third, the dew point temperature increases, for a given conversion, as the selectivity of the product increases to higher molecular weight polyamines. By monitoring variables which affect these parameters, one can maintain vapor phase conditions under reaction conditions. These rules are perhaps self-evident but they permit one to readily use the information in the drawings to develop specific processes embraced within the scope of the invention.

If one prefers not to calculate reactor conditions necessary for vapor phase conditions, one can use physical characteristics of the process to make that determination. The latter technique, though may require some experimentation. One of the easiest methods for determining whether liquid or mixed phase conditions exist in the reactor is to monitor reactor product composition. For example if a phosphorus catalyst is used high levels; e.g., greater than 20 ppm catalyst levels occur, in the reaction product indicate the presence of some liquid phase. This is because of the solubility of the catalyst in the reactant and products. An increasing pressure drop or modification of catalyst structure, e.g. rounded corners of pellets, etc. will also reveal this feature if some liquid phase is present. If such conditions exist the ammonia level or reaction temperature must be increased if below 275° C. or the pressure decreased if above 75 psig.

Generally, the level of ammonia used in the reaction at the temperature and pressure specified will be from 2 to 20, and preferably is 4–12 moles per mole of alkanolamine; e.g., monoethanolamine. The molar ratio of alkylenediamine to alkanolamine; e.g., ethylene diamine to monoethanolamine, will be from 1 to 5:1.

The following examples are provided to illustrate various embodiments of the invention as well as illustrate some of the differences between the process described herein and other processes utilized in the prior art.

EXAMPLE 1

Catalyst A Preparation

Lanthanum nitrate hexahydrate (130 g, 0.30 mole) was dissolved in deionized water (150 ml) with stirring. Diammonium hydrogen phosphate (79.2 g, 0.60 mole) was dissolved in deionized water (140 ml) with stirring. While a solution of diammonium hydrogen phosphate was vigorously stirred, the solution of lanthanum nitrate was added in one portion over a period of 5 to 10 seconds. A thick, lumpy precipitate formed immediately. After 10 minutes of manual stirring, a thick, creamy suspension resulted. Vacuum filtration to isolate the precipitate was started within one-half hour of the time of addition of the solutions. Complete separation of the filtrate required 5 to 6 hours, owing to the very finely divided nature of the precipitate. The resulting pasty solid was washed sequentially with three 100 ml portions of deionized water. After washing, the filter cake was dried at 80°–90° C. to constant weight to afford 113 g of a lanthanum acid phosphate (Catalyst A).

Catalyst B Preparation

The above procedure was repeated using the corresponding ammonium dihydrogen phosphate—(86.25 g (0.75 mole) in 300 ml deionized water) and lanthanum nitrate hexahydrate—(108.25 g (0.25 mole) in 150 ml deionized water) solutions in place of the ammonium hydrogen phosphate and lanthanum nitrate solutions to obtain 60 g of a second lanthanum acid phosphate (Catalyst B).

The intent of the above-described lanthanum acid phosphate catalyst preparations is to provide a general procedure to prepare the desired Group IIIB metal monohydrogen phosphate or dihydrogen phosphate. However, phosphate-containing materials may be obtained which consist predominantly of the Group IIIB metal phosphate, the Group IIIB metal monohydrogen phosphate, the Group IIIB metal dihydrogen phosphate, or mixtures in varying proportions of the Group IIIB metal mono- and dihydrogen phosphate, and/or mixtures in varying proportions of any of the above Group IIIB metal acid phosphates with the Group IIIB metal phosphate. Such variations in catalyst composition may result from complicated dependence of the catalyst composition on preparation conditions, such as temperature, concentration of reagents, stoichiometry of reagents, rate and order of reagent addition, pH of preparation, duration of preparation, volume and pH of waterwash, duration of catalyst washing, and duration and temperature of catalyst drying. In any event, the Group IIIB metal acid phosphates obtained according to the general preparations described above for lanthanum acid phosphates are catalytically active as exemplified for the production of polyamines in the following examples.

EXAMPLE 2

A series of reactions were carried out under various operating conditions. In those instances where vapor phase conditions were utilized or attempted, the reaction was carried out in a stainless steel packed bed reactor filled with solid phase catalyst pellets. The feeds were introduced into the top of the reactor and the reactants passed downflow over the catalyst bed. The reaction product was withdrawn from the bottom of the reactor as a vapor. The pressure was maintained in the reactor by a backpressure regulator.

Table 1 provides a description of the reaction conditions for producing polyethylene polyamines and such conditions include the usage of various catalysts, reaction temperatures, pressures, liquid hourly space velocity (LHSV), mole ratio of ammonia to monoethanolamine to ethylene diamine, reaction times (where appropriate) and various comments with respect to whether liquid phase conditions occurred or where high catalyst concentrations occurred in the reaction product.

Table II provides the results in terms of the quantities of various components in the reaction product in weight percent. The analysis was done by the use of gas chromatography. Lanthanum acid phosphate refers to lanthanum mono and dihydrogen phosphate.

TABLE I

| Run | Catalyst | Reaction Temp. °C. | PSIG Press. | LHSV | Mole Ratio Feed $NH_3$ | MELA | EDA | Phosphate Content (ppm) | Comments |
|---|---|---|---|---|---|---|---|---|---|
| 1 | Lanthanum Acid Phosphate-A | 265 | 1400 | 1.5 | 6.9 | 1 | 1 | 32.2 | Liq. phase |
| 2 | Lanthanum Acid Phosphate-A | 255 | 1400 | 1.5 | 4.6 | 1 | 1 | 141.3 | Liq. phase |
| 3 | Lanthanum Acid Phosphate-B | 245 | 300 | 1.5 | 12 | 1 | 2 | | Gas phase |
| 4 | Lanthanum Acid Phosphate-B | 225 | 300 | 1.0 | 12 | 1 | 2 | | Gas Phase |
| 5 | Lanthanum Acid | 255 | 200 | 3.0 | 8 | 1 | 2 | | Gas phase |

TABLE I-continued

| Run | Catalyst | Reaction Temp. °C. | PSIG Press. | LHSV | Mole Ratio Feed NH₃ | MELA | EDA | Phosphate Content (ppm) | Comments |
|---|---|---|---|---|---|---|---|---|---|
| | Phosphate-B | | | | | | | | |
| 6 | Lanthanum Acid Phosphate-B | 255 | 200 | 3.0 | 4 | 1 | 2 | | Gas phase |
| 7 | Rare Earth Acid Phosphateˢ-B | 225 | 300 | 1.0 | 12 | 1 | 2 | | Gas phase |
| 8 | Lanthanum Acid Phosphate/Alumina | 250 | 250 | 2.1 | 8 | 1 | 2 | | Gas phase |
| 9 | 34% $H_3PO_4$ on Silica | 250 | 250 | 3.0 | 4 | 1 | 2 | 14.25 | Mixed Phases |
| 10 | Lanthanum Acid Phosphate/Alumina | 250 | 250 | 2.6 | 4 | 1 | 2 | | Mixed Phase |
| 11 | 34% $H_3PO_4$ on Silica | 230 | 248 | 2.2 | 8 | 1 | 2 | | Gas Phase |
| 12 | 34% $H_3PO_4$ on Silica | 255 | 300 | 1.5 | 11 | 1 | 2 | | Gas phase |
| 13 | 34% $H_3PO_4$ on Silica | 260 | 250 | 2.0 | 12 | 1 | 4 | | Gas phase |
| 14 | Lanthanum Acid Phosphate-B | 299 | 302 | 1.33 | 11.6 | 1 | 2 | | Gas phase |
| 15 | Lanthanum Acid Phosphate-B | 300 | 302 | 3.01 | 11.6 | 1 | 2 | | Gas phase |
| 16 | $H_3PO_4$ | 250-350 | See comments | — | 0 | Not specified, appears to be 2:1 EDA:MELA | | | "pressure sufficient to provide a reaction mixture in a liquid phase; which is usually from about 200 to about 2500 psig." European Patent 93,983 |
| 17 | $(Et_2N)_3P$ | 250-350 | See comments | — | 0 | | | | "pressure sufficient to provide a reaction mixture in a liquid phase; which is usually from about 200 to about 2500 psig." European Patent 93,983 |
| 18 | $(Et_2N)_3P$ | 250-350 | See comments | — | 0 | | | | "pressure sufficient to provide a reaction mixture in a liquid phase; which is usually from about 200 to about 2500 psig." European Patent 93,983 |
| 19 | $(Et_2N)_3P$ | 250-350 | See comments | — | 0 | | | | "pressure sufficient to provide a reaction mixture in a liquid phase; which is usually from about 200 to about 2500 psig." European Patent 93,983 |
| 20 | Lanthanum Acid Phosphate-B | 255 | 200 | 1.5 | 12 | 1 | 2 | | Vapor phase |
| 21 | Lanthanum Acid Phosphate-B | 255 | 200 | 1.5 | 8 | 1 | 2 | | Vapor phase |
| 22 | Boron Phosphate | 250-400 | 14.7 | 1.56-3.35* | 0 | 1 | 1 | | Vapor phase, prior art. U.S. Pat. No. 4,036,881 |
| 23 | Boron Phosphate | 300 | 1500 | 0.59 | 0 | 1 | 1 | | Liquid phase, prior art. U.S. Pat. No. 4,036,881 |

LHSV based on EDA/MELA only.
*Based on EDA, MELA, and nitrogen. Mole ratio of nitrogen to equmolar EDA/MELA feed not specified.

TABLE II

| RUN | PIP | AEP | DETA | TETA (NC) | TETA (C) | TEPA (NC) | Sel (NC) | % Conversion |
|---|---|---|---|---|---|---|---|---|
| 1 | 3.06 | 4.32 | 50.38 | 17.00 | 1.34 | 15.07 | 83 | 43 |
| 2 | 2.38 | 0.89 | 64.85 | 12.95 | 0.00 | 0.00 | 78 | 27 |
| 3 | 4.13 | 7.27 | 51.49 | 14.46 | 9.26 | 5.28 | 71 | 29 |
| 4 | 6.03 | 13.07 | 53.30 | 9.63 | 3.30 | 0.00 | 67 | 17 |
| 5 | 3.87 | 6.86 | 55.67 | 14.78 | 5.63 | 1.50 | 72 | 33 |
| 6 | 3.95 | 6.31 | 53.64 | 15.25 | 3.60 | 8.11 | 77 | 38 |
| 7 | 5.80 | 6.88 | 65.58 | 4.35 | 1.63 | 0.00 | 70 | 11 |
| 8 | 2.57 | 6.37 | 43.78 | 16.52 | 8.32 | 11.31 | 72 | 36 |
| 9 | 3.52 | 4.71 | 45.99 | 14.80 | 3.56 | 12.37 | 72 | 33 |
| 10 | 3.12 | 5.38 | 45.99 | 17.17 | 4.64 | 12.68 | 76 | 35 |
| 11 | 3.93 | 5.83 | 46.60 | 12.71 | 4.30 | 9.35 | 69 | 19 |
| 12 | 3.26 | 7.04 | 45.28 | 16.35 | 8.83 | 9.68 | 71 | 57 |
| 13 | 2.38 | 5.03 | 56.61 | 15.53 | 7.85 | 7.24 | 79 | 68 |
| 14 | 9.69 | 19.73 | 22.21 | 6.97 | 16.75 | 0.56 | 29.75 | 96.34 |
| 15 | 6.11 | 15.64 | 36.15 | 10.96 | 16.51 | 2.70 | 49.81 | 86.58 |
| 16 | 4.35 | 1.15 | 77.20 | 4.88 | 0.00 | 0.00 | 82.08 | 29.3 |
| 17 | 2.87 | 2.27 | 71.68 | 8.36 | 3.46 | 0.00 | 79.24 | 37.7 |
| 18 | 3.01 | 1.37 | 73.90 | 8.50 | 2.09 | 0.00 | 81.61 | 37.1 |
| 19 | 3.40 | 1.53 | 72.84 | 9.86 | 3.45 | 0.16 | 81.18 | 43.5 |
| 20 | 3.23 | 9.63 | 47.69 | 11.65 | 14.82 | 2.15 | 61.5 | 46.2 |
| 21 | 3.65 | 8.42 | 48.97 | 13.07 | 13.24 | 4.06 | 66.2 | 47.9 |
| 22 | a | a | a | a | a | a | a | a |

TABLE II-continued

| RUN | PIP | AEP | DETA | TETA (NC) | TETA (C) | TEPA (NC) | Sel (NC) | % Conversion |
|---|---|---|---|---|---|---|---|---|
| 23 | 8.50 | 6.50[b] | 71.70 | 13.2[c] | 13.2[c] | — | >71.70 | 35.40[d] |

PIP = piperazine
AEP = N(2-aminoethyl)piperazine
DETA = diethylene triamine
TETA (NC) = triethylene triamine (noncyclic)
TETA (C) = triethylene triamine (cyclics)
TEPA (C) = tetraethylene pentamine (cyclic isomers)
TEPA (NC) = tetraethylene pentamine (noncyclic isomers)
Conversion is based on MELA.
[a]Not specified by U.S. Pat. No. 4,036,881; products are described as "complex and highly cyclic".
[b]Includes 2-(hydroxyethyl) piperazine.
[c]Isomer distribution not specified.
[d]Based on EDA and MELA.

The data show that a variety of catalyst systems can be used to effect intermolecular condensation of monoethanolamine. Under proper control conversion can be from 40-60% (see Runs 12-13 at high selectivity). Runs 22 and 23, which exemplify the prior art show high selectivity at low conversion. In fact, selectivity is not much higher than in Runs 12-13 and conversion is much lower. The data also show that as one raises the pressure and moves from gas phase to liquid phase the phosphate content in the reaction product rises dramatically. The product included catalyst and must be removed prior to product sale. Note Runs 2 and 5.

What is claimed is:

1. In a process for preparing a noncyclic polyalkylene polyamine which comprises contacting:
   (a) ammonia,
   (b) an alkyleneamine compound having two primary amino groups of the general formula:

wherein R is hydrogen or a lower alkyl ($C_1$-$C_4$) radical, x is a number from 2 to about 6, and y is a number from 1 to about 4, and (C) an alkanolamine compound having primary or secondary hydroxyl groups of the general formula:

wherein R is hydrogen or a lower alkyl ($C_1$-$C_4$) radical, x is a number from 2 to about 6, and y is a number from 0 to about 3; in the presence of an effective amount of an acidic catalyst and at a reaction temperature and reaction pressure sufficient to effect reaction between the ammonia, alkanolamine compound, and the alkyleneamine compound, the improvement for effecting said reaction under vapor phase conditions while maintaining high selectivity which comprises:
   establishing a reaction zone containing a catalytic bed comprising a solid phase acidic catalyst;
   contacting said bed with reactant ammonia, alkanolamine compound and alkyleneamine, and
   maintaining sufficient ammonia in the reaction zone such that the dew point temperature of the reactor contents is below the reaction temperature at reaction pressure.

2. The process of claim 1 wherein the catalyst comprises a phosphorus containing compound compounded into a particulate material or carried upon a support.

3. The process of claim 2 wherein the phosphorus containing compound is selected from the group consisting of acidic metal phosphates, phosphoric acid compounds and their anhydrides, phosphorus acid compounds and their anhydrides, alkyl or aryl phosphate esters, alkyl or aryl phosphite esters, alkyl or aryl substituted phosphorus acids, rare earth metal hydrogen phosphates, and phosphoramides.

4. The process of claim 3 wherein the alkanolamine is monoethanol amine.

5. The process of claim 4 wherein said alkyleneamine is ethylene diamine.

6. The process of claim 5 wherein the reactor temperature is from 200° to 285° C.

7. The process of claim 6 wherein the pressure is maintained from about 75 to 275 psig.

8. The process of claim 7 wherein the mole ratio of ethylene diamine to monoethanolamine is from about 1 to 5:1.

9. The process of claim 8 wherein the mole ratio of ammonia to monoethanolamine is from 2 to 20:1.

10. The process of claim 9 wherein the phosphorus-containing compound is present in an amount from 1 to 85% by weight of said catalyst.

11. The process of claim 10 wherein said phosphorus containing catalyst is a phosphoric acid and is supported on silica, alumina, zeolite, or carbon.

12. The process of claim 10 wherein said phosphorus containing catalyst contains a rare earth metal acid phosphate and said rare earth metal is a Group IIIB metal.

13. The process of claim 12 wherein said Group IIIB metal is lanthanum.

14. The process of claim 11 wherein the liquid hourly space velocity of monoethanolamine and ethylenediamine is from about 0.05 to 50.0 hr$^{-1}$.

15. The process of claim 1 wherein said solid phase acidic catalyst is a rare earth metal ion or hydrogen ion exchanged zeolite.

16. The process of claim 15 wherein the alkanolamine is monoethanol amine.

17. The process of claim 16 wherein the alkyleneamine is ethylene diamine.

18. The process of claim 17 wherein the reactor temperature is from 200° C. to 285° C.

19. The process of claim 18 wherein the mole ratio of ethylene diamine to monoethanolamine is from 1 to 5:1.

20. The process of claim 19 wherein the mole ratio of ammonia to monoethanolamine is from 2 to 20:1.

21. The process of claim 1 wherein said acidic catalyst is an inorganic sulfur or nitrogen containing salt or acid.

22. The process of claim 21 wherein said inorganic sulfur or nitrogen containing catalyst is nitric acid or sulfuric acid.

23. The process of claim 21 wherein the alkanolamine is monoethanol-amine.

24. The process of claim 23 wherein said alkyleneamine is ethylene diamine.

25. The process of claim 24 wherein the reactor temperature is from 200° C. to 285° C.

26. The process of claim 25 wherein the pressure is maintained from about 50 to 275 psig.

27. The process of claim 26 wherein the mole ratio of ethylene diamine to monoethanol amine is from about 1 to 5:1 and the mole ratio of ammonia to monoethanolamine is from about 2 to 20:1.

28. A process for preparing a noncyclic polyalkylene polyamine which comprises:
(a) contacting an alkanolamine compound having a primary amino group and a primary or secondary hydroxyl group of the general formula where R is hydrogen or a lower alkyl ($C_1$–$C_4$) radical, x is a number from 2 to 6, and y is a number from 0 to 3, with ammonia and an alkyleneamine compound having two primary amino groups of the general formula:

where R is hydrogen or a lower alkyl ($C_1$–$C_4$) radical, x is a number from 2 to 6, and y is a number from 1 to 4, in the presence of a catalytically effective amount of a supported phosphoric acid catalyst at a temperature from about 225° C. to about 255° C. and a pressure from 50 to 275 psig and a sufficient amount of ammonia in the reaction zone to reduce the dew point of the reactor contents to a temperature below said reaction temperature, said ammonia being present in an amount from 2 to 20 moles per mole alkanolamine.

29. The process of claim 28 in which the alkanolamine is monoethanolamine, the alkylene amine is ethylene diamine, the liquid hourly space velocity of monoethanolamine and ethylene diamine is from 0.05 to 50 hr.$^{-1}$, the phosphoric acid content of the catalyst is from 1 to 85% by weight of the catalyst.

* * * * *